(12) United States Patent
Lomask et al.

(10) Patent No.: US 7,104,962 B2
(45) Date of Patent: Sep. 12, 2006

(54) COUGH/SNEEZE ANALYZER AND METHOD

(75) Inventors: Joseph Lomask, Wilmington, NC (US); Richard A. Larson, North Warnborough (GB)

(73) Assignee: Buxco Electronics, Inc., Sharon, CT (US)

( * ) Notice: Subject to any disclaimer, the term of this patent is extended or adjusted under 35 U.S.C. 154(b) by 0 days.

(21) Appl. No.: 10/872,255

(22) Filed: Jun. 18, 2004

(65) Prior Publication Data

US 2004/0267150 A1    Dec. 30, 2004

Related U.S. Application Data

(60) Provisional application No. 60/480,875, filed on Jun. 24, 2003.

(51) Int. Cl.
*A61B 5/08*    (2006.01)

(52) U.S. Cl. ................................................ 600/529

(58) Field of Classification Search .................. 600/538
See application file for complete search history.

(56) References Cited

U.S. PATENT DOCUMENTS

| 4,368,740 | A | | 1/1983 | Binder |
| 4,413,620 | A | * | 11/1983 | Tucker ........................ 128/869 |
| 5,513,648 | A | * | 5/1996 | Jackson ....................... 600/529 |
| 5,562,101 | A | | 10/1996 | Hankinson et al. |
| 5,622,164 | A | | 4/1997 | Kilis et al. |
| 5,705,735 | A | | 1/1998 | Acorn |
| 6,168,568 | B1 | * | 1/2001 | Gavriely ...................... 600/529 |
| 6,436,057 | B1 | | 8/2002 | Goldsmith et al. |
| 6,723,055 | B1 | * | 4/2004 | Hoffman ....................... 600/538 |

* cited by examiner

*Primary Examiner*—Charles A. Marmar, II
*Assistant Examiner*—Patricia Mallari
(74) *Attorney, Agent, or Firm*—MacCord Mason PLLC

(57) ABSTRACT

A cough event is differentiated from a sneeze event of a test subject enclosed within a plethysmograph test chamber by measuring air pressure changes during the event, and comparing the pressure changes against criteria indicative of a cough to determine the likelihood that the event is a cough. Air pressure changes are recorded as pressure and/or sound values. A graphical record of a waveform of changes in the air pressure during an event relative to a baseline value is recorded, and a value is calculated that is indicative of the likelihood that the event is a cough based on the sizes of areas between the waveform and baseline during the event, said areas including a first area indicative of the change in air pressure during air inspiration, a second area indicative of the change in air pressure during air compression, and a third area indicative of the change in air pressure during expiration.

19 Claims, 5 Drawing Sheets

COUGH/SNEEZE ANALYZER AND METHOD

The application claims the benefit of Provisional Application Ser. No. 60/480,875, filed Jun. 24, 2003.

BACKGROUND OF THE INVENTION (1) Field of the Invention

The present invention relates to an apparatus and method for distinguishing a cough from a sneeze, and in particular to an apparatus and method of comparing the sound and volume attributes of possible cough events by a test subject within a plethysmograph against evaluation criteria to ascertain which events are probably coughs.

(2) Description of the Prior Art

The affects of various gases and aerosols on test subjects, e.g., rats and mice, are determined in laboratory research by enclosing a test subject, e.g., a mouse or rat, in the test chamber of a laboratory testing device known as a plethysmograph. A gas or aerosol is introduced into the chamber and the respiratory patterns of the test subject are evaluated by measuring changes in the pressure within the test chamber.

Plethysmographs are comprised of a test chamber to enclose the test subject, a reference chamber, and a differential pressure transducer connected to the two chambers, e.g., via tubing extending from a port in each chamber to the transducer. Both chambers are in communication with the ambient air, i.e., the air within the room where the tests are being conducted, through inlet ports or pneumotachographs.

As changes to the air volume within the test chamber occur, pressure variations are recorded by the transducer, which normally displays the recorded data in numerical form or as a graph. Air pressure within the test chamber can also vary due to changes in the pressure of air entering the test chamber through the pneumotachographs. The transducer simultaneously measures variations in air pressures within the two chambers, and subtracts the reference chamber measurements from the animal chamber measurements. As a result, the net pressure variations are essentially attributable to the respiration patterns of the test animal. Preferably, the test and reference chamber pneumotachographs are close to each other to minimize variations in exterior air patterns.

A representative plethysmograph of the type used to measure small animal pulmonary responses is shown and described in commonly assigned U.S. Pat. No. 5,379,777 to Lomask, the entire disclosure of the patent being incorporated herein by reference.

One of the criteria measured is the number of time that the test animal coughs during a given time. The number of coughs can be measured to observation, with the tester listening for the coughs. However, this system is tedious, time consuming and inaccurate. Further, there is a degree of uncertainty due to the fact that a cough is often difficult to distinguish from a sneeze due to the similarity of their sound and their limited duration. Therefore, there is a need for an apparatus and method for automating the process of counting coughs during such experiments, and in particular for distinguishing between coughs and sneezes that occur.

SUMMARY OF THE INVENTION

The present invention is directed to an improved apparatus and method for measuring pressure changes within a test chamber of a plethysmograph resulting for coughs and sneezes by a test subject within the chamber, and to an apparatus and method for differentiating a cough from a sneeze.

Generally, a plethysmograph forming a part of the apparatus of the present invention is comprised of a test chamber to enclose the test subject, a reference chamber, air inlets or pneumotachographs, which are basically screen covered openings, are positioned in the housing wall to permit air to enter the test and reference chambers, and a pressure transducer in communication with the test and reference chambers. The test chamber also includes an air outlet that may be connected to a vacuum source to draw air through the test chamber, and an aerosol inlet connectible to a gas or aerosol source. The reference chamber is preferable proximate to the test chamber to minimize variations in external air conditions between the inlets of the two chambers. For example, the two chambers may be separated by a common wall.

The pressure transducer communicates with the two chambers through ports. For example, a block may be attached to the exterior wall of the plethysmograph with ports extending through the wall into the two chambers. Tubes may then extend from the ports to the transducer. The transducer is in turn connected to a recorder, usually through an amplifier, to record changes in air pressure, indicating changes in air volume. Simultaneous measurement of air changes within the reference chamber permits changes in exterior air pressure to be partially subtracted from the measured values. As a result, the recorded measurements largely reflect actual pressure changes created by the test subject within the test chamber.

The recorder is connected to an analyzer or processor equipped with software capable of evaluating the recorded changes in air pressure against predetermined criteria to ascertain which of the discharge events, the term being used herein to collectively describe coughs and sneezes, are to be determined to be coughs. While described herein for the sake of clarity and convenience as separate instruments, it will be understood by one skilled in the art that the recorder and processor may be joined in a single enclosure, or may be a single instrument that performs both functions.

Discrimination between a cough and a sneeze is possible due to the different pressure patterns resulting from the different events. During a cough, the test subject first inspires air from within the chamber in a normal breathing pattern. The pressure within the chamber increases during inspiration due to the warming and resultant expansion of the air within the animal's body, which expands within the chamber to increase the chamber pressure.

Following inspiration, but prior to a cough, the test subject's glottis is temporarily closed, preventing discharge of air from the subject's lungs. At the same time, the subject's muscles compress the air within the lungs, resulting in a decrease in chamber pressure due to the decreased displacement by the subject. The subject's glottis then opens, resulting in a rapid discharge of the air from the lungs into the chamber, and expansion of the air which is no longer compressed, resulting in an increase of chamber air pressure.

The same stages occur during a sneeze, but with significant differences. In sneeze, the discharge of the air is not blocked by closure of the glottis as it is during cough, resulting in a different time and volume profile. Finally, the discharged air results in a lower increase in pressure, since the air is compressed less and therefore expands less, during a sneeze as compared to a cough.

The sound of a cough is also different from the sound of a sneeze. Discharge event sounds can be recorded by using the transducer as a microphone, i.e., by recording the air pressure as sound. That is, the transducer can be in communication with a recorder adapted to record pressure changes as pressure values and as sound. Generally, the sound of a cough will be of a different frequency and duration from the sound of a sneeze. Therefore, it is possible to differentiate a cough from a sneeze by analyzing the recorded sounds against predetermined criteria.

Accuracy of the analysis is increased by combining two different factors in the pressure analysis. That is, the probabilities of the two criteria are added to produce a combined criteria value that is compared against a predetermined value to determine if a given event is a cough or a sneeze. It will be apparent that the cough/sneeze analysis can be used to determine when probable coughs occur and that such determinations can be combined with other recorded information to determine the frequency and number of such coughs.

DETAILED DESCRIPTION OF THE INVENTION

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

Figure 1:
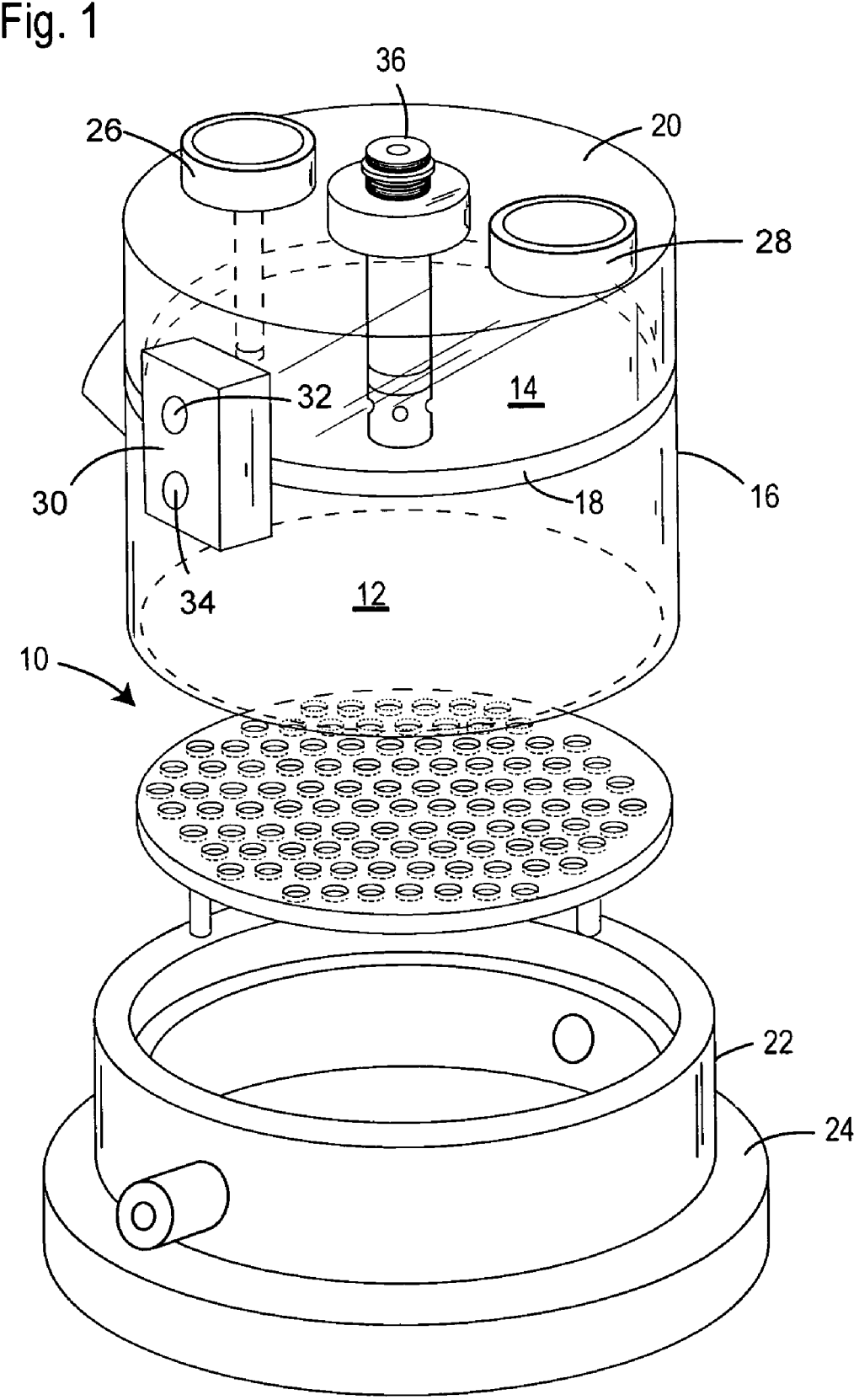
FIG. 1 is a perspective view of a prior art plethysmograph.

FIG. 1 illustrates a prior art plethysmograph, generally 10, that includes a test chamber 12 and a reference chamber 14. Chambers 12 and 14 share a common cylindrical wall 16 that is divided into the two chambers by a common separator wall 18. A top wall 20 covers reference chamber 14. The lower end of common wall 16 is fitted into a cylindrical base wall 22, which rests on a base 24. Test chamber pneumotach 26 is in communication with test chamber 12, while pneumotach 28 is in communication with reference chamber 14. Transducer block 30 is mounted on the outer surface of cylindrical wall 16 and spans separator wall 18. A first port 32 extends through block 30 to communicate with test chamber 12, while a second port 34 extends through block 30 to communicate with reference chamber 14. An aerosol manifold 36 is used to introduce gases or aerosols into test chamber 12.

Figure 2:
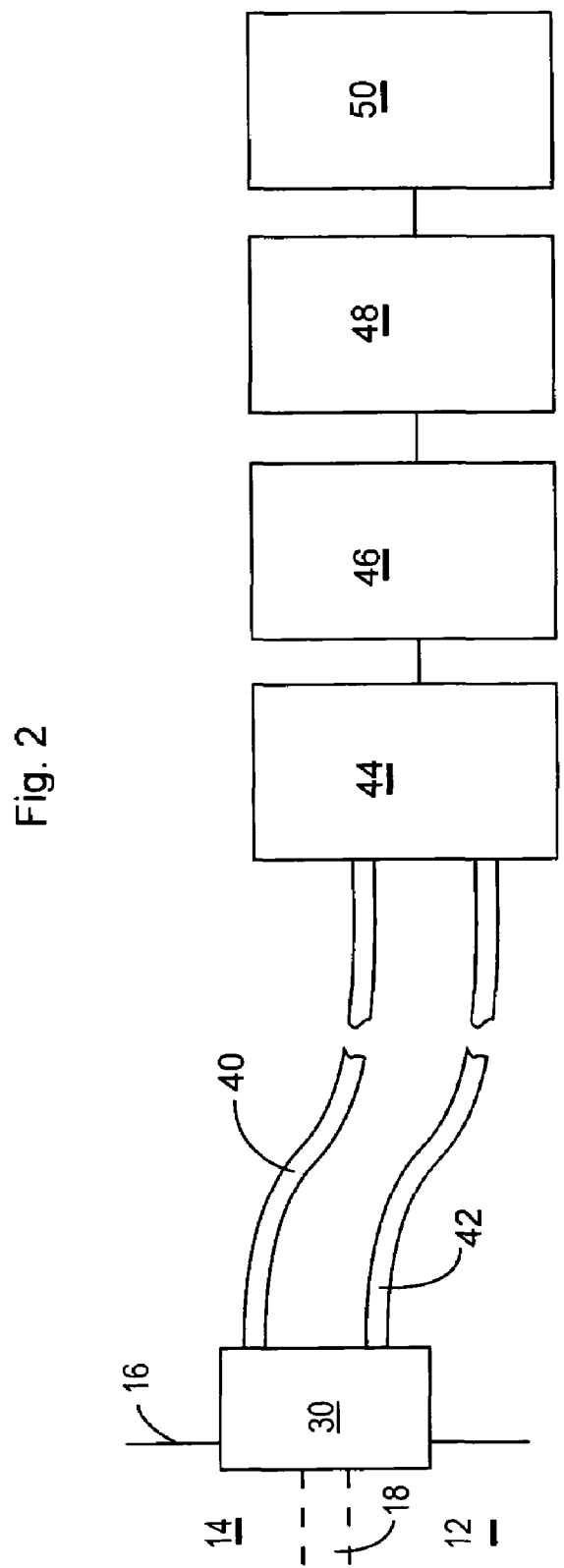
FIG. 2 is a schematic illustration of a plethysmograph transducer attached to a recorder through an amplifier, with the recorder being in communication with a data processor.

As illustrated schematically in FIG. 2, tubes 40 and 42 connect ports 32 and 34, respectively, to differential pressure transducer 44 to measure pressure changes. Transducer 44 is connected through amplifier 46 to a recorder 48, which is connected to data processor 50. Processor 50 includes software to evaluate recorded changes in air pressure against predetermined criteria to ascertain which of the discharge events, the term being used herein to collectively describe coughs and sneezes, are to be determined to be coughs. Recorder 48 and processor 50 may be joined in a single enclosure, or may be a single instrument that performs both functions.

The following table defines terms used in the following description and in the formulas:

| Term | Units | Description |
|---|---|---|
| V2wcThreshold | ml/kg | Value at which the V2wc parameter is 50% certain to be a cough. |
| DHPCThreshold | ms | Value at which the DHPC is 50% certain to be a cough |
| V2wcWeight | (1) | Relative importance of the V2 parameter in determining cough. |
| DHPCWeight | (1) | Relative importance of the DHPC parameter in determining cough. |
| V2wcCrispness | (1) | Relative sharpness of the transition of the V2wc values between events being considered coughs or sneezes. |
| DHPCCrispness | (1) | Relative sharpness of the transition of the DHPC values between events being considered coughs or sneezes. |
| Pessimism | [0.2, 0.8] | Relative pessimism in counting coughs. Low values are more optimistic (resulting in more events counted as coughs). High values are more pessimistic, and may miss counting coughs. |
| V1 | ml | Volume of air moved out of the plethysmograph corresponding to inspiration just prior to the event. |
| V2 | ml | Volume of air moved into the plethysmograph corresponding to compression inside the animal against its closed glottis. |
| V3 | ml | Volume of air released by reversal of air compressed, corresponding to re-expansion of compressed gas. |
| WT | g | Weight of the test subject. |
| V2wc | ml/kg | V2 corrected to the weight of the animal. |
| DHPC | ms | On the Pressure graph, the time from one half of the maximum in V2 to the time of one half of the minimum in V3. |
| fzyV2wc | (1) | Certainty value between 0 and 1 that the event is a cough, considering only the weight corrected value of V2. |
| fzyDHPC | (1) | Certainty value between 0 and 1 that the even is a cough considering only the DHPC parameter. |
| fzyIsCough | (1) | Possibility value from 0 to 1 that the event is a cough using combined criteria. 0 indicates event is not a cough; 1 indicates that the event is certainly a cough. |
| IsCough | (none) | A value of 1 or 0. 1 = cough; 0 = not a cough |
| CCnt | (none) | Total number of coughs since last analysis. |

Figure 3:
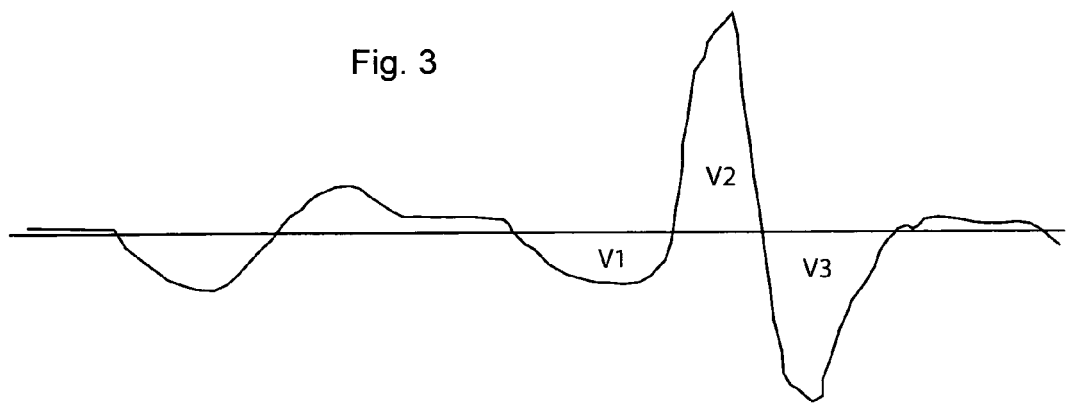
FIG. 3 is a graph of a waveform of pressure values.
Figure 4:
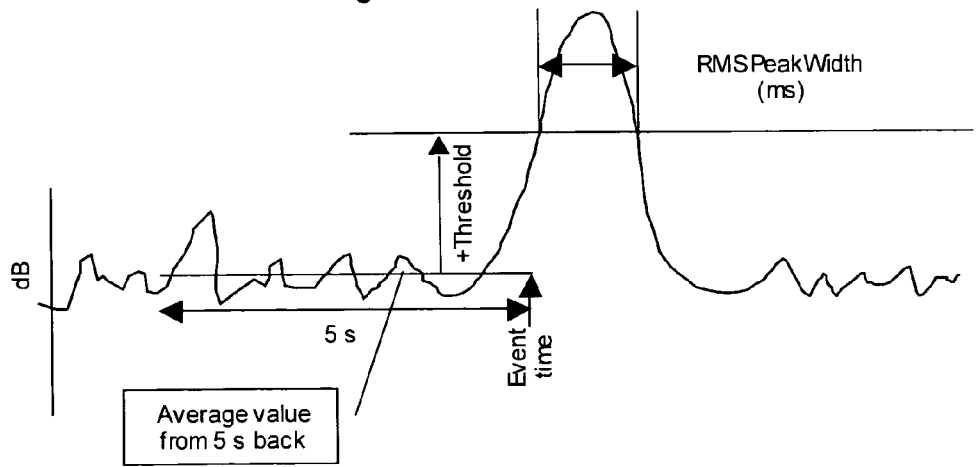
FIG. 4 is a graph of a sound waveform.

FIG. 3 is a representative waveform measured by transducer 44 relative to a baseline showing the values V1, V2 and V3 defined above. V2wc is calculated by the following formula:

$$V2wc = 1000 \cdot V2 / WT$$

After all the values above are computed, the information is processed in processor 50 to determine if the event was a cough or not, taking into consideration that V2wc and RMSPeakWidth both increase when the event is a cough. Fuzzy logic aids the decision.

Figure 5:
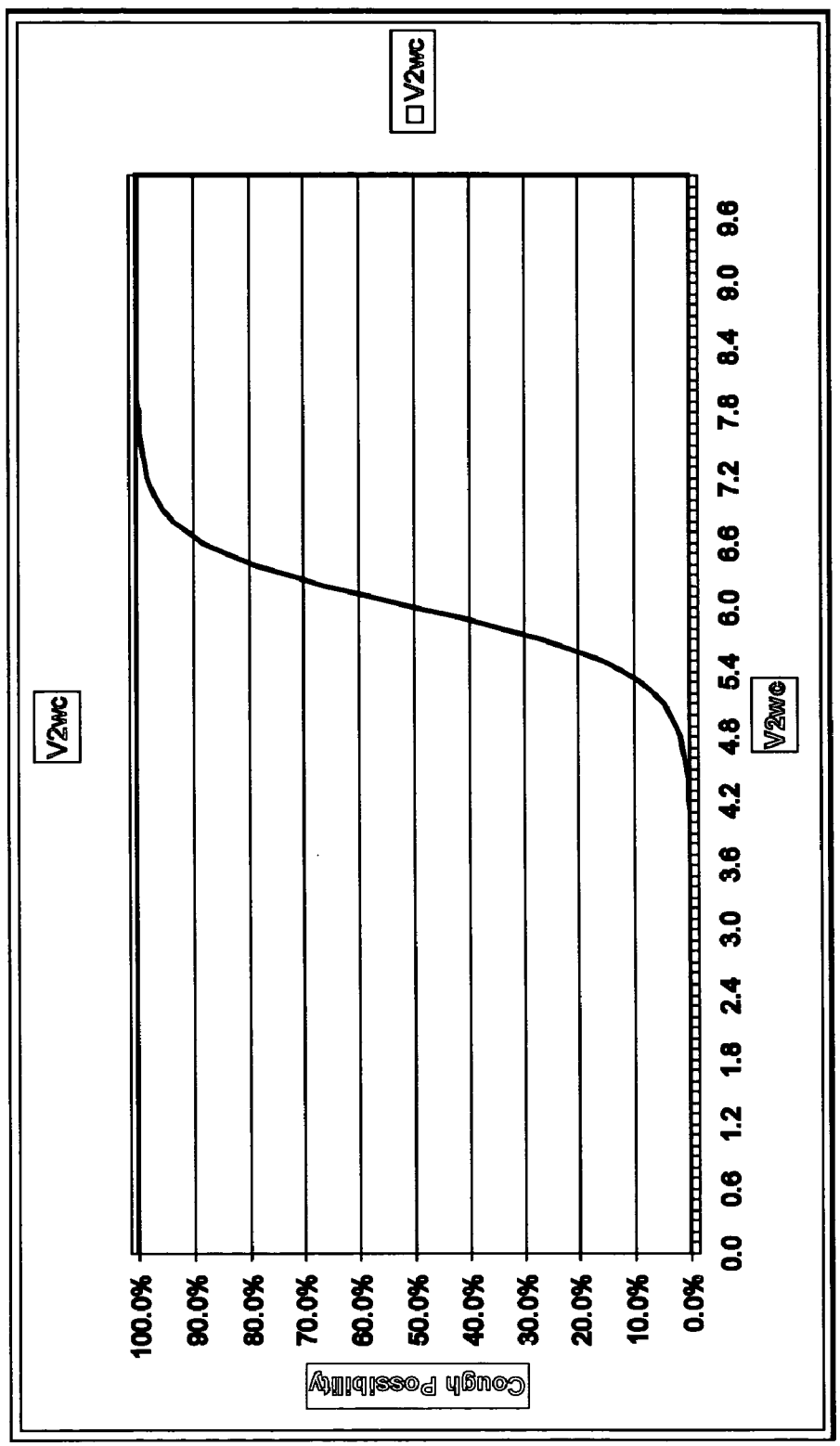
FIG. 5 is a graph of a computed pressure value.

A possibility value for the event in respect to V2wc is computed from the following formulae:

$$fzyV2wc = 1 - \frac{1}{1 + e^{V2b(V2wc - V2a)}} \text{ where}$$

$$V2a = V2wcThreshold$$

$$V2b = \frac{V2wcCrispness}{V2a}$$

fzyV2wc now gives a possibility value in the interval [0,1] based on the constants V2a and V2b. The profile of this curve is illustrated in FIG. 5, given V2a=5 and V2b=1.

fzyDHPC is calculated by the following formula:

$$fzyDHPC=1-1/(1+e^{\wedge}(DHPCb*(DHPC-DHPCa)))$$

where:
DHPCa=DHCPThreshold
DHPCb=DHPCCrispness/DHPCa

Figure 6:
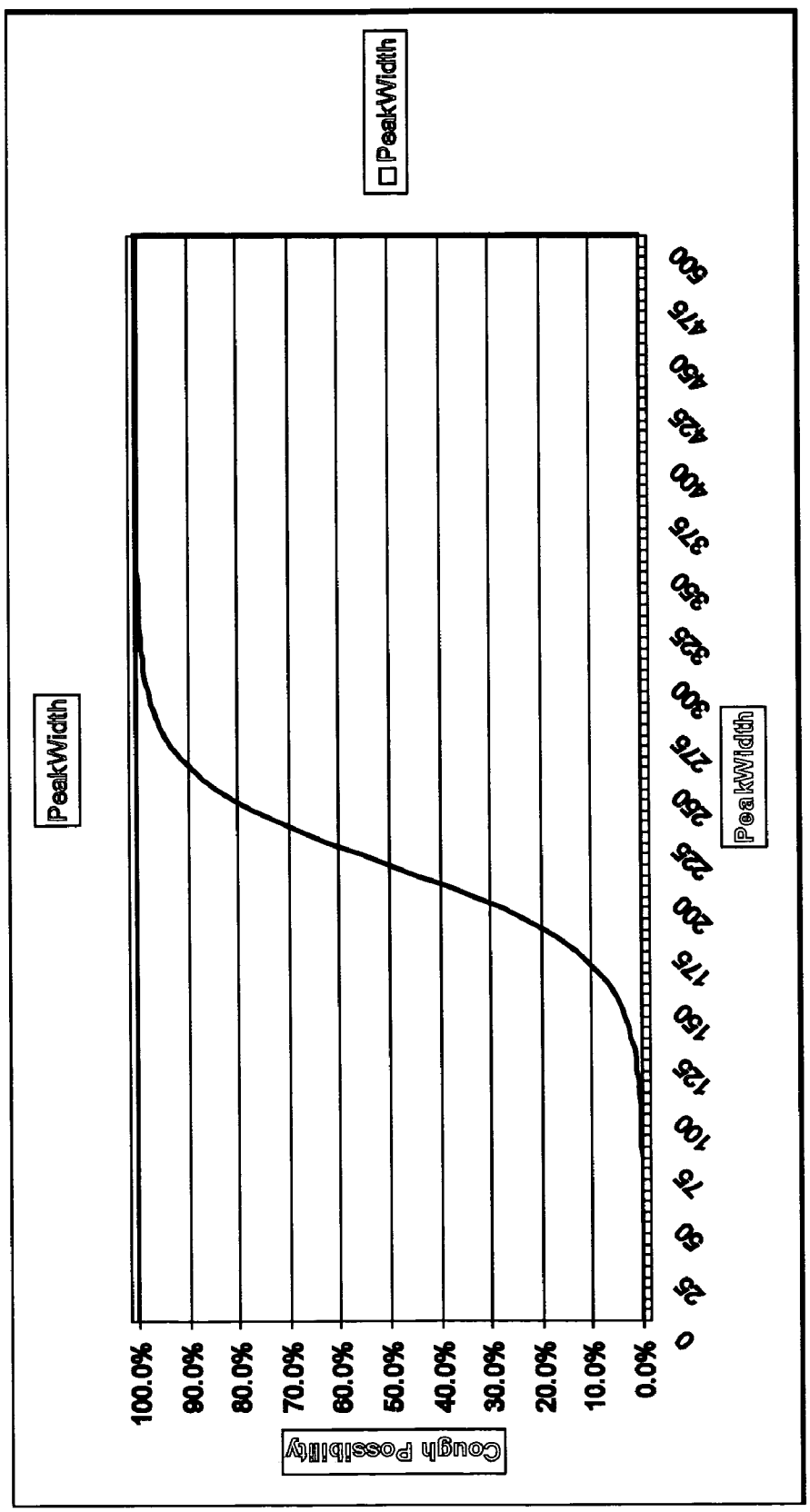
FIG. 6 is a graph of a computed sound value.

The resulting profile is illustrated in FIG. 6, given DHPCa=26 and DHPCb=0.0769.

The fzyV2wc and fzyDHPC parameters are added with weighting factors and then re-normalized to give a new combined possibility value, fzyIsCough by the following formula:

$$fzyIsCough=(fzyV2wc*V2wcWeight+fzyDHPC*DHPCWeight)/(V2wcWeight+DHPCWeight)$$

The final IsCough value is computed as a 1 or 0. If fzyIsCough>IsCoughThreshold then IsCough=1, otherwise it is 0.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A method of differentiating between a cough and a sneeze of a test subject within a plethysmograph test chamber comprising:
    a) measuring changes in the air pressure within the chamber during an event that is a cough or a sneeze; and
    b) comparing the parameters of the air pressure changes against parameters indicative of a cough to determine the likelihood that the event is a cough instead of a sneeze.

2. The method of claim 1, further including measuring the sound of the event and comparing the sound against criteria indicative of a cough.

3. The method of claim 1, wherein the pressure changes are measured with a differential pressure transducer.

4. The method of claim 1, wherein said plethysmograph includes a reference chamber, said pressure change being determined by comparing the pressure within the test chamber relative to the pressure within the reference chamber.

5. The method of claim 1, wherein changes in air pressure are measured during air inspiration, during air compression, and during expiration.

6. A method of differentiating between a cough and a sneeze of a test subject within a plethysmograph test chamber comprising:
    a) graphing a waveform of changes in the air pressure within the chamber during an event that is a cough or a sneeze relative to a baseline measurement;
    b) measuring the size of the areas between the waveform and baseline during the event;
    c) measuring the time between the waveform crossing certain thresholds; and
    d) comparing the sizes and times of threshold crossings of the measured areas against sizes and times of threshold crossings indicative of a cough to determine the likelihood that the event is a cough instead of a sneeze.

7. The method of claim 6, wherein said areas include a first area indicative of a waveform in air pressure during air inspiration, a second area indicative of a waveform in air pressure during air compression, and a third area indicative of a waveform in air pressure during expiration.

8. The method of claim 6, further including adjusting the step of comparing for the weight of the test subject.

9. The method of claim 6, further including measuring the timing between descending slopes of a portion of the waveform indicative of compressing and a subsequent portion of the waveform indicative of re-expansion.

10. The method of claim 6, wherein said waveform is measured with a differential pressure transducer.

11. The method of claim 6, wherein said plethysmograph includes a reference chamber, and wherein a pressure change is determined by comparing the pressure within the test chamber relative to the pressure within the reference chamber.

12. A method of differentiating between a cough and a sneeze of a test subject within a plethysmograph test chamber comprising:
    a) graphing a waveform of changes in the air pressure within the chamber during an event that is a cough or a sneeze relative to a baseline measurement;
    b) measuring the size of areas between the waveform and baseline during the event, said areas include a first area V1 indicative of a change in air pressure during air inspiration, a second area V2 indicative of a change in air pressure during air compression, and a third area V3 indicative of a change in air pressure during expiration;
    c) computing the parameter V2wc to adjust for weight of the test subject by the formula $$V2wc=1000 \cdot V2/WT$$

where WT is the weight of the test subject; and
    d) determining a volume possibility value fzyV2wc for the event by the formula $$fzyV2wc = 1 - \frac{1}{1 + e^{V2b(V2wc - V2a)}} \text{ where}$$

$$V2a = V2wcThreshold$$

$$V2b = \frac{V2wcCrispness}{V2a}$$

V2a and V2b are constants, V2wcThreshold is a value at which the V2wcparameter is 50% certain to be a cough, and V2wcCrispness is a relative sharpness of the transition of the V2wc values between events being considered coughs or sneezes, said volume possibility value being indicative of the likelihood that the event is a cough.

13. The method of claim 12, further including determining a sound possibility value fzyDHPC for the event by the formula $$fzyDHPC=1-1/(1+e^{\wedge}(DHPCb*(DHPC-DHPCa)))$$

where:
DHPCa=DHCPThreshold
DHPCb=DHPCCrispness/DHPCa

DHPC is the time from one half of the maximum of the pressure waveform in the are V2 to the time of one half of the minimum of the pressure waveform in the area V3, DHPCThreshold equals the value at which the DHPC timing is 50% certain to be a cough, and DHPCCrispness is a relative sharpness of the DHPC parameter in determining cough, said sound possibility value being indicative of the likelihood that the event is a cough.

14. The method of claim 13, wherein said volume and timing possibility values are combined to create a combined possibility value fzyIsCough by the formula $$fzyIsCough=(fzyV2wc*V2wcWeight+fzyDHPC*DHPCWeight)/(V2wcWeight+DHPCWeight)$$

where V2wcWeight equals the relative importance of the V2 parameter in determining cough, DHPCWeight equals the relative importance of the DHPC parameter in determining cough.

15. The method of claim 14, further including determining if the event is a cough by comparing fzyISCough to a threshold value.

16. An apparatus for differentiating between a cough event and a sneeze event of a test subject comprising:
 a) a plethysmograph having a test chamber for enclosing said test subject;
 b) a measurement means for measuring air pressure changes within said chamber;
 c) a recorder for recording changes measured by said measurement means; and
 d) a processor with installed software capable of calculating a value based on the pressure changes during an event indicative of the likelihood that the event is a cough.

17. The apparatus of claim 16, wherein said plethysmograph further includes a reference chamber, and said measurement means is a differential pressure transducer in communication with said test and reference chambers.

18. The apparatus of claim 16, wherein said recorder is adapted to record air pressure changes as pressure values and as sound.

19. The apparatus of claim 16, wherein said recorder is adapted to graphically record a waveform of changes in the air pressure within the chamber during an event relative to a baseline value, and said processor is adapted to calculate a value indicative of the likelihood that the event is a cough based on the sizes of areas between the waveform and baseline during the event, said areas including a first area indicative of a change in air pressure during air inspiration, a second area indicative of a change in air pressure during air compression, and a third area indicative of a change in air pressure during expiration.

* * * * *